(12) United States Patent
Smolsky

(10) Patent No.: US 7,397,380 B1
(45) Date of Patent: Jul. 8, 2008

(54) DEVICE AND METHOD FOR MONITORING STATE OF THERMAL COMFORT OF A BABY AT SLEEP OR A PARTIALLY DISABLED PATIENT

(75) Inventor: Michael Smolsky, 18 Short #3, Brookline, MA (US) 02446

(73) Assignee: Michael Smolsky, Brookline, MA (US)

( * ) Notice: Subject to any disclaimer, the term of this patent is extended or adjusted under 35 U.S.C. 154(b) by 387 days.

(21) Appl. No.: 10/904,245

(22) Filed: Oct. 30, 2004

Related U.S. Application Data

(60) Provisional application No. 60/481,589, filed on Oct. 31, 2003.

(51) Int. Cl.
G08B 23/00 (2006.01)

(52) U.S. Cl. .................. 340/573.1; 340/573.7; 600/474

(58) Field of Classification Search .............. 340/573.1, 340/573.4, 573.5, 573.7, 575, 550; 600/474, 600/549, 310, 315; 348/E5.09, 59; 250/252.1
See application file for complete search history.

(56) References Cited

U.S. PATENT DOCUMENTS

| | | | | |
|---|---|---|---|---|
| 4,403,251 A | * | 9/1983 | Domarenok et al. | 348/135 |
| 4,849,635 A | * | 7/1989 | Sugimoto | 250/342 |
| 5,272,340 A | * | 12/1993 | Anbar | 250/332 |
| 5,313,951 A | * | 5/1994 | Zhao | 600/474 |
| 5,999,843 A | * | 12/1999 | Anbar | 600/474 |
| 7,019,671 B2 | * | 3/2006 | Kawai | 340/937 |

* cited by examiner

Primary Examiner—Van T. Trieu

(57) ABSTRACT

Systems and methods for monitoring baby's or partially disabled patient's level of thermal comfort during his/her rest in bed are provided. Preferably, the system comprises: a sensor of infrared (IR) radiation coupled to electric circuitry, the circuitry includes a transmitter of radio signal, and, as a separate unit, a receiver of this radio signal. The transmitter includes a circuit containing an alarm with an adjustable threshold that turns the alarm on whenever the heat flux radiated by the body of a patient or a baby rises above user-adjustable upper threshold value, or falls below lower threshold value. The system may be combined with a standard, advanced or video baby monitor.

15 Claims, 4 Drawing Sheets

DEVICE AND METHOD FOR MONITORING STATE OF THERMAL COMFORT OF A BABY AT SLEEP OR A PARTIALLY DISABLED PATIENT

BACKGROUND OF THE INVENTION

1. Field of the Invention

The present invention relates in general to a baby/patient monitor, and in particular to a monitor capable of measuring flux of IR radiation emitted by body of a baby or a disabled patient.

2. Description of Related Art

Baby monitors are well known. A standard baby monitor consists of two physically separate units: a baby unit and a parent unit, each of which can be powered by a battery or an AC current source. The baby unit contains a microphone or other sound detecting device and is placed in a location near a baby. The parent unit contains a speaker and is placed in a location near the baby's guardian. A sound (e.g. a stirring or crying baby) detected by the baby unit is transmitted to the parent unit for output to the guardian to hear and respond to accordingly.

Several versions of this standard model exist. One of them involves a number of light emitting diodes (LEDs), which turn on in series to indicate a level of the sound measured by the microphone. This visual alert is useful when other noises may interfere with the receiver audio output.

In another version of the system the parent unit is capable of sending audible or other information to the baby unit, that provides means for comforting the baby without the need to approach him/her. Such baby monitors with soothing units are described by Fitzgerald, et al., U.S. Pat. No. 6,759,961, Altenhofen; Cynthia L, U.S. Pat. No. 6,043,747.

Some similar devices include enhancements, which allow monitoring other parameters relevant to baby's conditions, such as baby's movements or whether his/her clothes are dry (Xiaowei et al., patent CN2301724U). Some of these parameters may be related to baby's health conditions, such as heart beat and/or respiratory rates, as in cardiac and apnea monitoring system (Holland, et al., U.S. Pat. No. 6,764,451). Another example is a psychological monitor utilizing information obtained through measuring EKG of a baby (Mault, et al., U.S. Pat. No. 6,790,178). An invention documented by Jackson, III in U.S. Pat. No. 6,047,201 is designed to measure level of oxygen in infant's blood.

Pediatricians nowadays consider that an important factor in a very young child's life is ambient temperature and thus it is therefore necessary for the ambient temperature of the child's room to be taken into account, and for the appropriate changes to be made if the temperature rises or falls beyond suitable limits. The invention of Liu Chi Cheung et al., patent EP0983580 addresses this issue.

Other devices permanently display a live image of the baby. The image is acquired by a vide camera, built into the baby unit and is displayed on video screen built into the parent unit. Such a use of a wireless video camera coupled to a TV receiver is described in Ray; Rajarshi, U.S. Pat. No. 6,192,257, Strandwitz, et al., U.S. Pat. No. 6,522,352.

Remote temperature and heat flux measurements based on infrared (IR) technology are used for medical (e.g. I. Kushnir, U.S. Pat. No. 6,508,831), industrial (e.g. M. R. Clark, D. M. McCann and M C. Forde, "Application of IR thermography to the non-destructive testing of concrete and masonry bridges", NDT & E International, Volume 36, Issue 4, June 2003, Pages 265-275), agricultural (e.g. G. Wright, "IR images to reduce peanut aflatoxin risk", International CustomWire, Sep. 06, 2004, Item CX200425018851), military (e.g P. L. Martinez et al., "Improved Thermal Analysis of Buried Landmines", IEEE Transactions on Geoscience & Remote Sensing, September 2004, Vol. 42 Issue 9, p1965) and scientific (e.g. S. Montelpare and R. Ricci, "An experimental method for evaluating the heat transfer coefficient of liquid-cooled short pin fins using IR thermography", Experimental Thermal and Fluid Science, Volume 28, Issue 8, October 2004, Pages 815-824) applications. The way those proposed technologies are designed makes them inappropriate and/or too expensive for monitoring a baby or a patient at sleep.

Watabe, et al. suggested a way to improve accuracy of temperature/heat flux measurements using 2 IR sensors in U.S. Pat. No. 6,236,046. A similar technique is used in the preferred embodiment of the present invention.

Many parents cover their babies with a blanket or a comforter when the babies sleep. While adults often develop skills to cover/uncover themselves with the blanket in sleep as they feel too cold/warm, babies lack those skills till they reach the age of about 10 years old. Accidental movement of a baby during his/her sleep can therefore lead to his/her inadequate coverage by the blanket. In some cases under such circumstances the baby would wake up and call for a guardian, but this rarely happens instantaneously, and typically the baby would stay asleep while feeling thermal discomfort for some time. That could be a reason for bad dreams, diseases and even fatalities.

In particular, according to medical research, Sudden Infant Death Syndrome (SIDS) is one of the leading causes of post-neonatal mortality in industrialized countries. Substantial proportion of the SIDS deaths could be avoided by providing safe sleeping environment for infants, whereas their overheating is considered as one of the major risk factors (Ponsonby A L, Dwyer T, Cochrane J, New England Journal of Medicine (329(6) 1993; Mathews T J, Menacker F, MacDorman M F, National Vital Statistics Reports 52(2) 2003).

Some baby monitors were invented to specifically address the issue of SIDS. One of such devices is documented by Walton, U.S. Pat. No. 5,864,291. This monitor is attached to baby's torso in order to detect that the baby is no longer breathing and inform the parent of that. Another invention (Gibbon et al. patent WO9819596) alarms the baby's guardian of the fact that the baby's hear is no longer beating.

Additionally, because thermoregulatory neurons are synaptically linked to those regulating respiration, adequate temperature control (especially by infants) maintains normal respiration. Therefore, of particular importance may be the temperature control during sleep of patients with increased risk of asphyxia such as pre-term infants, babies and adults with physical and mental disabilities, as well as elderly patients (Scher M S, Steppe D A, Salerno D G, Beggarly M E, Banks D L, Clinical Neurophysiology 114(1)2003).

The device proposed addressees the issue of informing the guardian about a baby's or patient's thermal discomfort during his/her sleep, while being inexpensive in mass production and easy in use.

SUMMARY OF THE INVENTION

It is the first objective of the invention to provide a solution for monitoring the state of thermal comfort of a baby or partially disabled patient during his/her sleep. The system for measuring baby's/patient's thermal comfort comprises a baby unit and a parent unit. The baby unit comprises an IR sensor, focused at the baby's/patient's bed and sensor output processing circuit configurable by user-adjustable parameters, such as the level of its sensitivity. The measuring device also includes convenience tools used for choosing proper direction of the sensor, such as a source of visible low-intensity light, emitted within the sensor's sensitivity cone. The parent unit is connected to the baby unit through radio (RF) or another kind of a link. This parent unit sounds an audio/visual alarm whenever the amount of heat emitted by the body of a baby/patient being monitored falls outside user-adjustable thresholds.

It is the second objective of the invention to provide a convenient way for configuring sensitivity thresholds of the IR sensor of the baby unit. The thresholds are configured relatively to flux of IR radiation emitted by the baby/patient at the state of his/her thermal comfort.

Other and further aspects, features, and advantages of the present invention will be apparent from the following description of the presently preferred embodiments of the invention given for the purpose of disclosure.

DETAILED DESCRIPTION OF THE INVENTION

Figure 1:
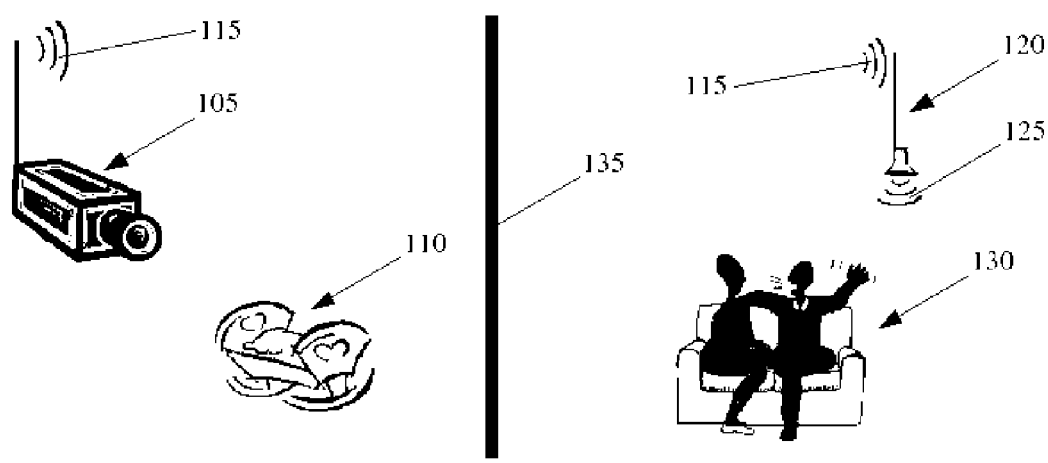
FIG. 1 illustrates a way of using the system; the baby unit is positioned of some distance, but on a direct line of sight of the baby and the parent unit is placed close to the baby's guardian.

The present invention provides a system that continuously measures IR flux from a human body. The system analyzes this flux by means of comparing it to user-tunable upper and lower thresholds and signals an audio and visual alarm whenever the flux falls outside these thresholds. The present system provides several advantages, including being small and inexpensive, it does not require physical contact with the human body and does not generate any harmful radiation.

SCIENTIFIC BACKGROUND OF THE INVENTION

In accordance with the $2^{nd}$ law of thermodynamics, a human body radiates certain amount of heat in order to function properly. Measurements show, that a naked human body under normal conditions (minimal activity, ambient temperature of 70-80° F., dry immobile air) radiates about 50 Wt/m² of heat. The skin of a healthy adult is capable of lowering its external temperature in order to be radiating similar amount of energy at even somewhat lower ambient temperatures, but this adjustment is accompanied by a feeling of thermal discomfort ("freezing"). The skin is also able to adapt to growth of ambient temperature above normal room temperature, while still radiating amount of energy close to the amount required. This is achieved by means of a different biological mechanism ("sweating"). Again, unpleasant feelings accompany the process of sweating. New-born babies (up to the age of about 1 month) can not adapt to changing thermal conditions as effectively as adults do, it is mostly the skin of the feet and palms of a new-born baby, that can effectively regulate its external temperature in response to changing ambient temperature.

In accordance with laws of thermodynamics and quantum physics, every object emits electromagnetic waves, known as thermal or "black body" radiation. Frequency spectrum and flux of energy transferred by these waves depend somewhat on color and structure of material the object is made of, but more importantly on its surface temperature. If that surface is at room temperature, typical frequency of the radiation is in IR (invisible for a human eye) part of the spectrum. Under the conditions being considered, other mechanisms of heat transport, such as convection or kinetic heat conductivity, play important roles in establishing heat balance between the body and ambient air. Effectiveness of all these mechanisms is usually in direct relationship to one another. It is therefore possible to measure heat transport due to IR radiation and predict overall heat loss of a body due to this and all other mechanisms altogether. The implementation of the present invention is based on measurement of IR flux being emitted by a human body. The temporal variations of this flux are used for determining changes in the state of thermal comfort of the body.

Advances in technology made measurement of energy flux from a human body possible and relatively inexpensive. Typically, an apparatus used for measuring flux of IR radiation comprises a semiconductor component combined with an optical subsystem needed for focusing the radiation at the sensitive part of the component and an electric circuit. Such an apparatus converts the energy of the radiation into electric current, which is typically amplified and analyzed using standard and specialized techniques.

DESCRIPTION OF THE PREFERRED EMBODIMENT

In one embodiment of the present invention there is provided a system comprising an IR sensor device, reflective optics and electric circuit coupled to the sensor device (all of those together are referred to as a "baby unit" in the description to follow), as well as a physically separate electronic block (to be referred to as a "parent unit").

FIG. 1 depicts typical usage of the system. Baby unit 105 is constantly measuring and analyzing heat flux emitted by sleeping baby 110. Once the flux falls outside user-configurable thresholds, baby unit 105 transmits radio waves 115 to parent unit 120. The thresholds are configured relatively to some predefined flux. This predefined flux corresponds to the radiation emitted by baby's 110 body at the state of thermal comfort. Parent unit 120 emits audible signal 125, which parents 130 of baby 110 can hear and respond to accordingly. The radio signal 115 can penetrate a wall 135 separating the baby 110 and the parents 130. Depending on local conditions, the parent unit 120 can be within the radius of about a few hundred feet from the baby unit 105.

OVERVIEW OF THE DESIGN OF THE EMBODIMENT

Figure 2:
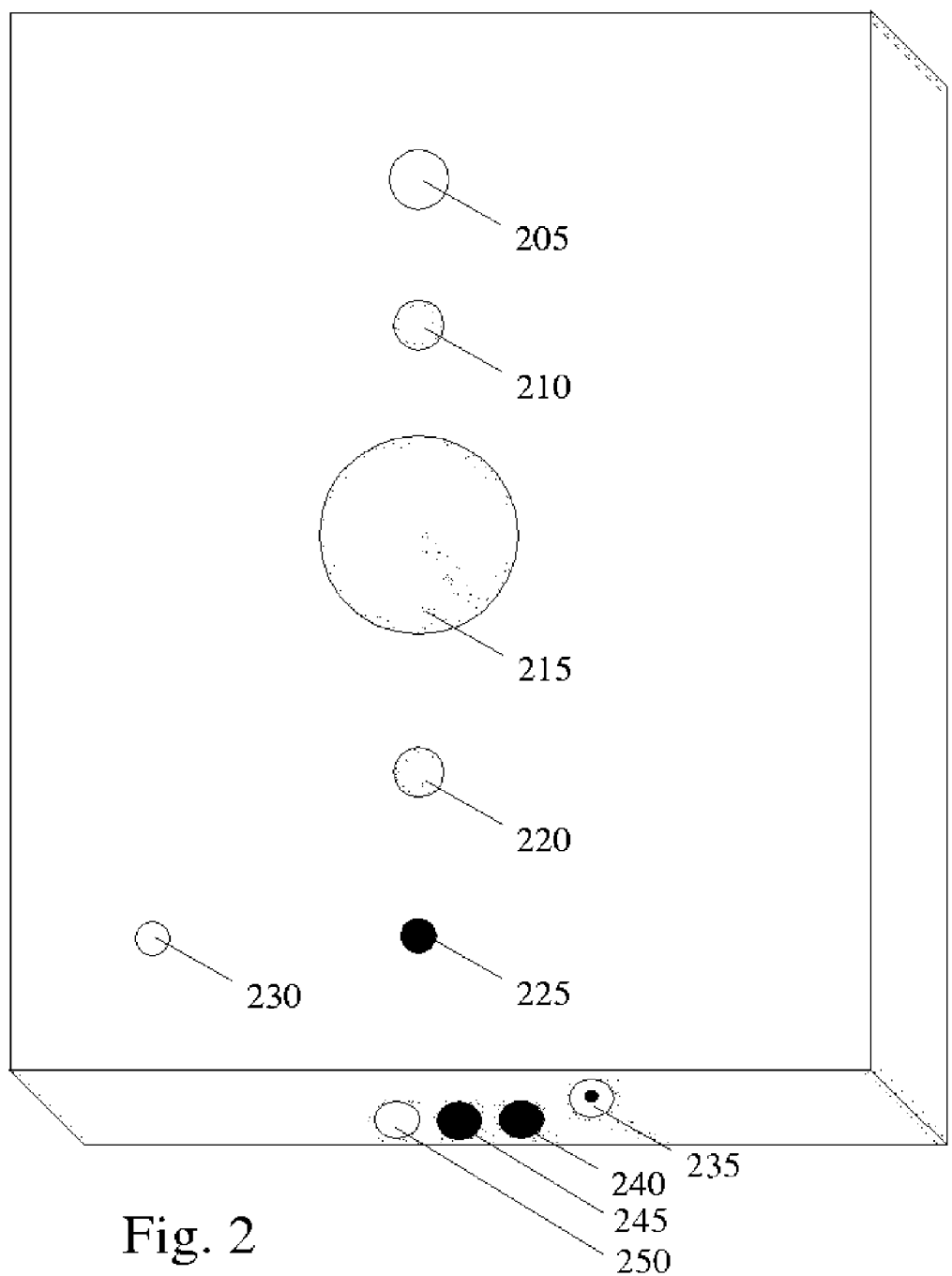
FIG. 2 depicts a general view of the preferred embodiment of the baby unit.

Refer to FIG. 2 for general view of the preferred embodiment of the baby unit 105. The following components are designated by numbers on the drawing: IR sensor 205; sensitivity switch 210; sensitivity knob 215; flash light switch 220; flash light 225; not ready indicator 230; DC in socket 235; overheating indicator 240; overcooling indicator 245; signal transmission indicator 250.

Figure 3:
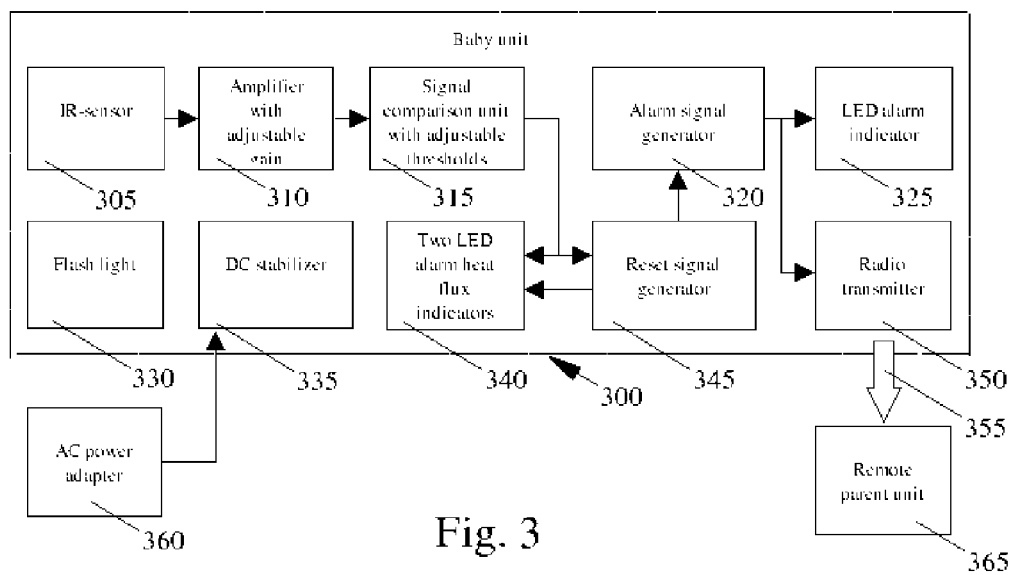
FIG. 3 is the signal flow chart of the preferred embodiment, main units of the preferred embodiment are presented as blocks, arrows designate flow of information within the device.

FIG. 3 depicts signal flow chart of the preferred embodiment of the invention. The blocks of the detector provide the following functionalities:

Baby unit 300 incorporates components in a single plastic box.

IR sensor 305 receives IR radiation and converts it into electric current. The radiation passes through an optical filter on its way to sensor 205. The bandwidth of the filter is designed to filter out radiation with spectral characteristics different from those typical for thermal radiation of a human body. Typical amplitude of electric signal generated by the sensor is 0.1-2 mV.

Amplifier with adjustable gain 310 amplifies the signal at one of two levels of the gain, to be selected by the user (using sensitivity switch 210). The amplitude of electric signal at the output of the amplifier 310 is 0.1-1 V. Besides providing signal amplification, amplifier 310 also filters out its high- and low-frequency components. The cutoff frequencies of the filter are determined by the range of speeds of the human body's motion, which the device is designed to detect (typically a few Hz).

Signal comparison unit with adjustable thresholds 315 compares the strength of the signal to the upper and lower thresholds. The thresholds are adjusted by the user. Sensitivity knob 215 is used for this adjustment.

Alarm signal generator 320 provides a 2 sec long signal required for the initiation of transmission of the signal to the receiver (part of remote parent unit 365).

LED alarm indicator 325 (yellow) signals "not ready" state of the device.

When flash-light 330 is turned on (using flash light switch 220), the domain which the sensor is capable of measuring the heat flux from is illuminated by visible light. The user can adjust the position and the orientation of the heat flux detector in order to match this domain to the position of the baby's/patient's body in the process of installation of the device.

DC stabilizer 335 provides stable low-noise DC current at +6 V to other components of baby unit 300.

Indicators 340 display the state of the system on the face of baby unit 300 for additional convenience. When lit up, two of them (green/red LED) indicate that the IR flux exceeds lower/upper radiation thresholds, respectively.

Reset signal generator 345 responds to output of signal comparison unit 315. It feeds alarm signal generator 320. It also blocks radio transmitter 350 for about 15 sec in order to drive the amplifier with adjustable gain 310 into its waiting state. That blocks the possible influence of the radio transmitter 350 over amplifier 310.

Radio transmitter 350 generates an RF signal to be received by remote receiver (part of parent unit 365).

Radio waves 355 transmit the signal from radio transmitter 350 to radio receiver within the parent unit 365.

AC power adapter 360 (optional) supplies power to baby unit 300.

When remote parent unit 365 receives radio signal 355 generated by radio transmitter 350, either audio and/or light alarm indication is turned on to be noticed by the guardian. The receiver is portable and runs off an autonomous power supply (battery), which allows taking it hundreds of feet away from the transmitter.

Design of Electric Circuit of the Baby Unit

Figure 4:
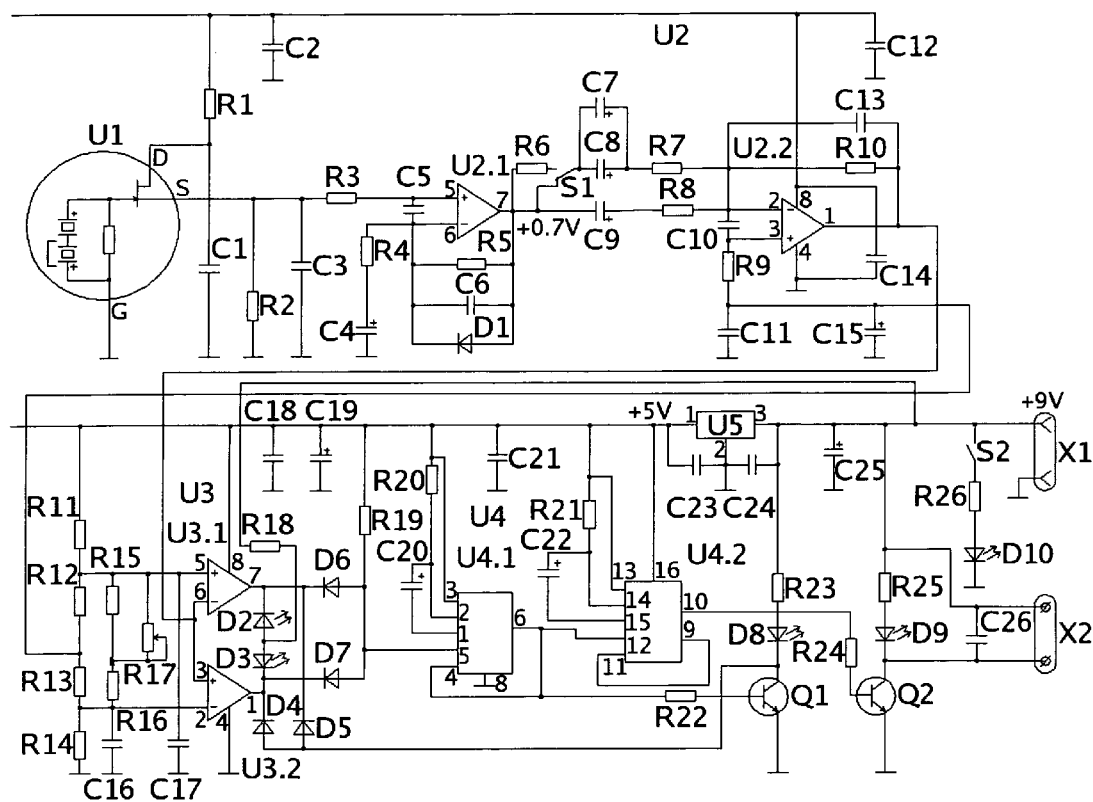
FIG. 4 is the principal circuit diagram of the baby unit of the preferred embodiment.

FIG. 4 depicts principle circuit diagram of the heat flux detector.

IR sensor 305 (U1) is sealed in a metal box with a window, transparent to far-IR part of the spectrum only. Only one of the two IR-detectors included in the sensor is exposed to light incoming through the window, while the other is used for thermal compensation, R1 and R2 define operating mode of the sensor. C1, C2, C3 suppress RF noise.

The two-stage amplifier 310, U2 is based on industry-standard linear IC and provides gains of 370 or 1100, depending on the state of the switch S1. Low and high cutoff frequencies of the amplifier are 0.05 Hz and 2.2 Hz, respectively. R4, R5, C4, C6 define the gain of the first stage of the amplifier U2.1 as well as its frequency response. R3 and C5 suppress external noise. D1 reduces the duration of power-up cycle of the amplifier. R7, R8, R10 and C7, C8, C8, C13 define the gain of the second stage of the amplifier U2.2, as well as its frequency response. R6 suppresses transient effects due to switching of S1. R9 defines DC mode of operation of the amplifier U2.2. C10, C11, C15 suppress external noise. The gains of both stages of the amplifier are 34 and 11 or 33 respectively, the latter depending on the state of the switch S1. Cutoff frequencies of both stages are the same. Thermal stability of the amplifier is achieved by filtering out DC component from the signal.

The signal comparison unit with adjustable thresholds 315 is based on a twin comparator U3. The two subunits U3.1 and U3.2 detect increase of the signal over the upper and its decrease below the lower thresholds, respectively. R11-R17 (R17 is a user-tunable rheostat) define the upper and lower thresholds relatively to the mean amplitude of the signal. Deviations of the two thresholds from the mean amplitude of the signal are implied to be at the same. C16, C17 suppress external noise. R9 guarantees equality of sensitivities of the amplifier in the cases of the increase or decrease of the signal with respect to the average.

The signal comparison unit with adjustable thresholds 315 feeds the reset signal generator 345 U4.1 after passing the signal through D6, D7 and R19. R20 and C20 specify the duration of the pulse (15 sec).

The alarm signal generator 320 U4.2 forms a pulse for the duration of 2 sec (specified by R21 and C22), which opens the cascade of Q2 through R24. The signal is fed into the leg X2 of the radio transmitter 350. C26 is used to suppress the noise.

The LED alarm indicator 325 D9 is connected in parallel to the radio transmitter 350. R25 specifies the current to flow through D9.

LEDs D2 (red) and D3 (green) 340 indicate the state (above the upper threshold, and below the lower threshold respectively) of the comparison unit. R18 specifies the current to flow through the LEDs. LED D8 (yellow) signals "not ready" state of the sensor, it's lit for the duration of the pulse generated by U4.1 through Q1 or by comparison units U3.1, U3.2 through D4 and D5, respectively. R22 limits the base current of Q1. R23 specifies the current through D8.

Ultra-bright LED 330, D10 is used for the illumination of sensitivity domain of the sensor. S2 switches the LED on and off. R26 specifies the current through D10.

The device is powered through X1. Stabilizer 335, U5 is used for suppressing the noise of the external a/c power adapter 360. C23, C24 guarantee the stability of U5. C2, C12, C14, C18, C21, C19, C25 are used to suppress the noise.

A 3$^{rd}$ party auto-pager implements the transmitter-receiver blocks 350, 355, 365 of the embodiment.

Combining the System with Standard and Advanced Baby Monitors

The system described can be combined with a standard or advanced baby monitor for providing even greater convenience for the user. In particular, the baby unit of the preferred embodiment may be combined with the baby unit of a standard/advanced baby monitor, while the parent unit of the embodiment may be combined with the parent unit of a standard/advanced baby monitor. In that case a single system carries out the functions of both the standard/advanced baby monitor as well as of the thermal comfort monitor being described as the preferred embodiment: the system transmits the information on the thermal comfort from the baby/patient to the parent/guardian as well as any noises in the vicinity of the baby/patient location. In a similar manner the system can also be combined with a wireless closed circuit TV system. In that case the parent/guardian is able to visually inspect the condition of the baby/patient and better evaluate the need to approach him/her, even if the thermal comfort monitor signals an alarm. The preferred embodiment can be combined with a comforting baby monitor, capable of sending parent's/guardian's voice back to the baby.

While there has been shown and described what are considered at present to be the preferred embodiments of the present invention, it will be appreciated by those skilled in the art that modifications of such embodiments may be made. It is therefore desired that the invention not be limited to these embodiments and it is intended to cover in the appended claims all such modifications as fall within the true spirit and scope of the invention.

Table 1 Summary of electronic components, used in the heat flux detector of the preferred embodiment

| Identifier of the component | Description of the component |
| --- | --- |
| R1-R4 | Resistors 100 KOm, 0.125 W |
| R5, R6, R10 | Resistors 3.3 MOm, 0.125 W |
| R9 | Resistor 1.5 MOm, 0.125 W |
| R7 | Resistor 150 KOm, 0.125 W |
| R8, R20, R21 | Resistors 300 KOm, 0.125 W |
| R11-R14 | Resistors 200 KOm, 0.125 W |
| R15 | Resistor 330 KOm, 0.125 W |
| R16 | Resistor 43 KOm, 0.125 W |
| R17 | Rheostat ~470 KOm |
| R18, R23, R25 | Resistors 1 KOm, 0.125 W |
| R19, R22, R24 | Resistors 10 KOm, 0.125 W |
| R26 | Resistor 270 Om, 0.25 W |
| C2, C11, C12, C14, C16-C18, C21, C23, C24, C26 | Capacitors 0.1 uF |
| C4, C15, C19, C25 | Capacitors 33 uF, 16 V |
| C6, C13 | Capacitors 22 nF |
| C7-C9 | Capacitors 10 uF |
| C22 | Capacitors 20 uF |
| C20 | Capacitor 100 uF |
| D1, D4-D7 | Diodes 1N3063 |
| D2 | LED, red L53- H |
| D3 | LED, green L53- G |
| D8, D9 | LED, yellow L53- Y |
| D10 | Bright LED L93SRC- E |
| Q1, Q2 | Transistors 2N2368 |
| U1 | IR-sensor IRA-E410ST1 |
| U2 | Linear IC LM358N |
| U3 | Comparator LM393N |
| U4 | Monostable multivibrator HCF4098 |
| U5 | Stabilizer 78L06 |
| S1, S2 | Switches |

What is claimed is:

1. A system comprising:
   a sensor device sensitive to temporal variations of flux of infrared (IR) radiation emitted by a human body, said variations measured relatively to a predefined reference flux of said radiation, said reference flux is the IR flux, emitted at a body's thermal comfort state;
   a transmitter device coupled to said sensor device and producing a signal for
   a receiver device, capable of displaying said variations of said flux of said radiation.

2. A system of claim 1, also equipped with a source of human-visible light, which, when turned on, illuminates the special domain, being monitored by said sensor device.

3. A system of claim 1, in which said receiver device is connected to said transmitter device via a radio RF link.

4. A system of claim 1, which is supplemented with a standard or advanced baby monitor system, said transmitter device is supplemented with the baby unit of the baby monitor device, and said receiver device is supplemented with the parent unit of the baby monitor system.

5. A system of claim 4, in which said baby unit is responsive to receiving a signal representative of an audible sound transmitted by said baby unit.

6. A system of claim 5, in which said baby unit transmits signals representative of an audible sound only when loudness of said sound is above a predefined threshold.

7. A system of claim 5, in which said baby unit is also responsive to receiving a signal representative of an audible sound transmitted from said parent unit.

8. A system of claim 7 in which said parent unit transmits signals representative of an audible sound only when loudness of said sound is above a predefined threshold.

9. A system of claim 1, which is supplemented with a closed circuit video link, CCTV, said transmitter device of the system is supplemented with a video camera, and said receiver device is supplemented with a video display responsive to the video camera for displaying real-time video images.

10. A method of monitoring a human employing a parent unit and a baby unit, said baby unit including an infrared sensor device coupled to transmitting electric circuit, said parent unit including receiving electric current, said method comprising the steps of:
    installing and configuring the system;
    receiving the infrared flux emitted by said human said infrared sensor device;
    converting said flux into an electric signal by said transmitting electric circuit;
    processing of said electric signal by said transmitting electric circuit; said processing comprising:
        comparing said electric signal to a signal corresponding to a flux emitted by said human in a state of thermal comfort;
        sending the result of said comparison to said receiving electric circuit; and activating said parent unit.

11. A method of claim 10, in which the step of processing of said electric signal includes comparison of said signal to some predefined upper and/or lower thresholds.

12. A method of claim 11, in which sending said result of said comparison by said transmitting electric circuit to said receiving electric circuit takes place only when said result of said comparison falls beyond said thresholds.

13. A method of claim 10 in which said step of activating said parent unit includes producing an audio output.

14. A method of claim 10 in which said step of activating said parent unit includes producing a visual output.

15. A method of claim 10 in which said step of installing the system includes usage of a human-visible light illuminating the domain of sensitivity of said sensor device and built-in said baby unit.

* * * * *